(12) United States Patent
Ohta et al.

(10) Patent No.: US 7,777,192 B2
(45) Date of Patent: Aug. 17, 2010

(54) CASSETTE SYSTEM

(75) Inventors: Yasunori Ohta, Kanagawa (JP); Eiichi Kito, Kanagawa (JP); Tsuyoshi Tanabe, Kanagawa (JP); Takuya Yoshimi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/230,772

(22) Filed: Sep. 4, 2008

(65) Prior Publication Data

US 2009/0060127 A1 Mar. 5, 2009

(30) Foreign Application Priority Data

Sep. 5, 2007 (JP) ............................. 2007-230767
Jul. 30, 2008 (JP) ............................. 2008-195690

(51) Int. Cl.
*G01T 1/24* (2006.01)

(52) U.S. Cl. ................................... 250/370.09

(58) Field of Classification Search ............ 250/370.08, 250/582, 336.1, 370.09; 378/169
See application file for complete search history.

(56) References Cited

U.S. PATENT DOCUMENTS

| | | | | |
|---|---|---|---|---|
| 4,534,076 A | * | 8/1985 | Barge | ............................. 5/147 |
| 5,328,019 A | * | 7/1994 | Boutet et al. | ................. 198/624 |
| 5,678,303 A | * | 10/1997 | Wichmann | .................... 29/806 |
| 5,773,839 A | * | 6/1998 | Krepel et al. | ................ 250/580 |
| 6,044,131 A | * | 3/2000 | McEvoy et al. | ............. 378/162 |
| 6,344,652 B1 | * | 2/2002 | Shoji | ...................... 250/370.09 |
| 7,126,129 B2 | | 10/2006 | Yamamoto | |
| 7,429,737 B2 | * | 9/2008 | Wojcik et al. | ........... 250/370.09 |
| 7,495,226 B2 | * | 2/2009 | Jadrich et al. | ........... 250/370.09 |
| 2002/0181659 A1 | * | 12/2002 | Watanabe et al. | ............ 378/189 |
| 2003/0042418 A1 | * | 3/2003 | Yamamoto | ................ 250/336.1 |
| 2003/0063708 A1 | * | 4/2003 | Shoji et al. | .................... 378/154 |
| 2004/0079908 A1 | * | 4/2004 | Ohkubo | ....................... 250/582 |
| 2004/0169150 A1 | * | 9/2004 | Nakajo | ..................... 250/484.4 |
| 2004/0252613 A1 | * | 12/2004 | Iwakiri | ..................... 369/53.12 |
| 2006/0017028 A1 | * | 1/2006 | Ohara et al. | ................. 250/582 |
| 2006/0054822 A1 | * | 3/2006 | Tsuchino | ................. 250/336.1 |
| 2006/0054839 A1 | * | 3/2006 | Yonekawa | ................ 250/484.4 |
| 2006/0097177 A1 | * | 5/2006 | Yamamoto | ............. 250/370.08 |
| 2006/0169907 A1 | * | 8/2006 | Shinden | .................. 250/370.09 |
| 2007/0165785 A1 | * | 7/2007 | Watanabe et al. | ............ 378/189 |

FOREIGN PATENT DOCUMENTS

| | | |
|---|---|---|
| JP | 07-140255 | 6/1995 |
| JP | 2000-105297 | 4/2000 |
| JP | 2003-248060 | 9/2003 |
| JP | 2004-173907 | 6/2004 |

* cited by examiner

*Primary Examiner*—David P Porta
*Assistant Examiner*—Djura Malevic
(74) *Attorney, Agent, or Firm*—Jean C. Edwards, Esq.; Akerman Senterfitt

(57) ABSTRACT

A lightweight cassette system comprises a cassette for detecting radiation image and a control unit for communicating with a console, the control unit being connected to the cassette. The control unit, which includes electronic components such as an interface circuit, a cassette controller, and a communication unit, is separably connected to the cassette which includes a radiation detector by connectors and a cable.

17 Claims, 12 Drawing Sheets

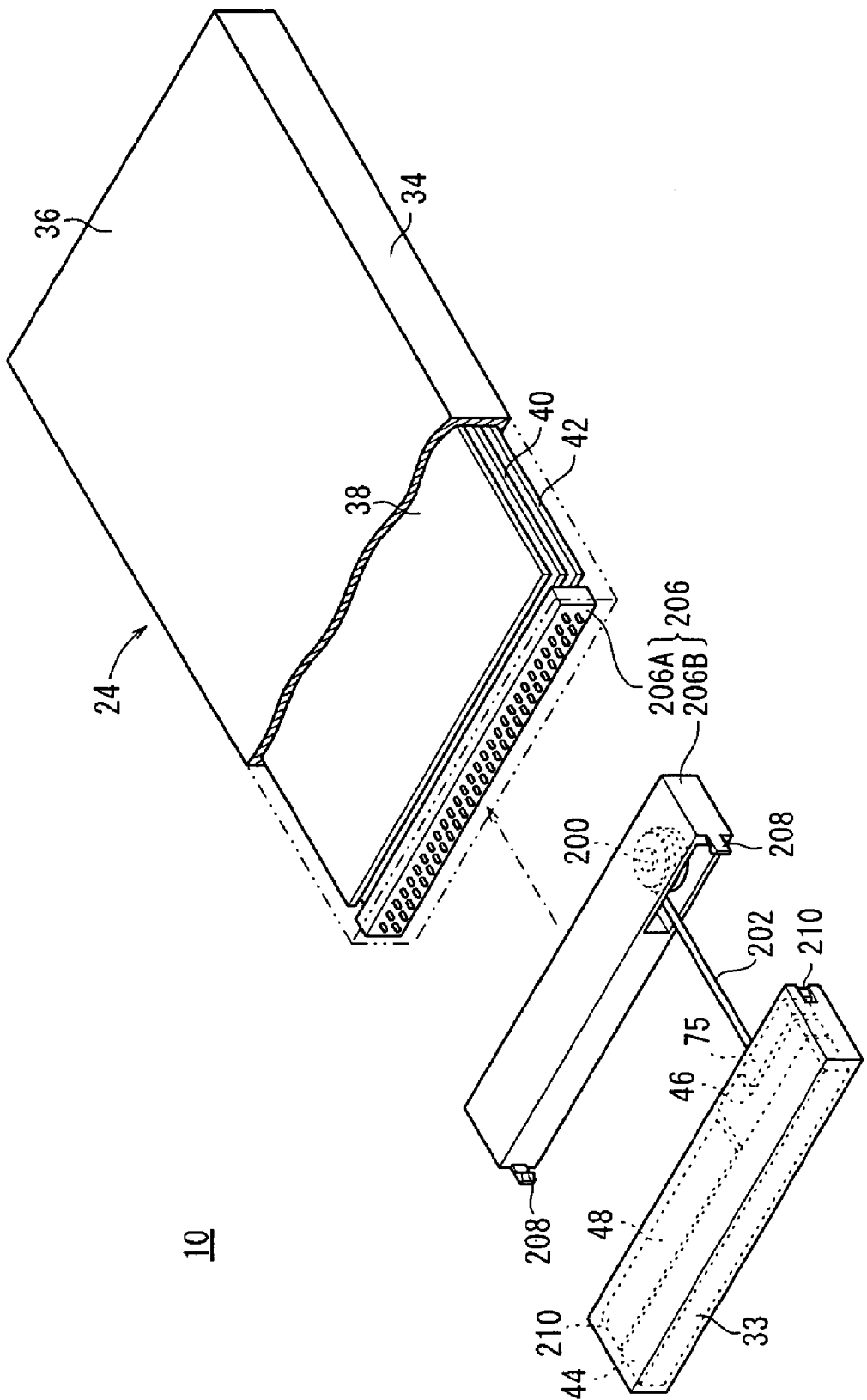

CASSETTE SYSTEM

CROSS-REFERENCE TO RELATED APPLICATIONS

The present application claims priority from Japanese Patent Application Nos. 2007-230767, filed Sep. 5, 2007, and 2008-195690, filed Jul. 30, 2008, the contents of both of which are herein incorporated by reference in their entirety.

BACKGROUND OF THE INVENTION

1. Field of the Invention

The present invention relates to a cassette system having a radiation detector for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation detector so as to capture a radiation image from the radiation. Known forms of the radiation detector include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read the radiation image as a visible image.

In the operating room or the like, it is necessary to read a recorded radiation image immediately from a radiation detector after the radiation image is captured for the purpose of quickly and appropriately treating the patient. As a radiation detector which meets such a requirement, there has been developed a radiation detector having a solid-state detector for converting a radiation directly into an electric signal or converting a radiation into visible light with a scintillator and then converting the visible light into an electric signal to read out a detected radiation image.

As shown in FIG. 12 of the accompanying drawings, Japanese Laid-Open Patent Publication No. 2004-173907 discloses a cassette (electronic cassette) 306 which is connected to a cable 302 having a connector 300 and has a battery 304, an image memory 305, and an electric board 303 on which a drive circuit, an amplifier, an A/D converter, and a serializing circuit are mounted. It also discloses an X-ray image capturing system in which a connector 310 on a cable 308 or a wireless module 330 is connected to the connector 310, a controller 314 with a power supply 312 is connected to the connector 300 by the cable 308 or a wireless terminal 322, and an X-ray generator 318 having an X-ray tube 317 is connected to the controller 314 by a cable 316. The controller 314 is combined with a monitor 320 for displaying captured images and a storage 338 for storing captured images.

The technology disclosed in Japanese Laid-Open Patent Publication No. 2004-173907 is undesirable because the cable 302 connected to the cassette 306 is awkward when the cassette 306 is carried around.

Japanese Patent No. 3494683 discloses a cassette which transmits captured radiation image information to a controller by way of wireless communications. According to the technology disclosed in Japanese Patent No. 3494683, no cable is connected to the cassette.

According to Japanese Patent No. 3494683, no cable is connected to the cassette since image data are transmitted from the cassette to the controller by way of wireless communications. However, when the cassette communicates with the controller after the cassette is set between a patient to be imaged and a bed on which the patient lies, if the directivity of an antenna of the cassette and the directivity of an antenna of the controller are not aligned with each other, then the transmission and reception sensitivity of the cassette and the controller is greatly reduced. One solution is to increase the intensity of a radio wave transmitted from the antenna of the cassette. The increased intensity of the radio wave transmitted from the antenna of the cassette necessarily results in an increase in the power consumption of the cassette. Particularly, after the cassette disclosed in Japanese Patent No. 3494683 is set between the patient and the bed, it is difficult to change the orientation of the cassette for increasing the transmission and reception sensitivity of the cassette and the controller. If the patient on the bed is seriously ill or an aged person, then it is all the more difficult to change the orientation of the cassette. There is no disclosure in Japanese Laid-Open Patent Publication No. 2004-173907 with respect to the above difficulties.

Japanese Laid-Open Patent Publication No. 2003-248060 discloses a cassette comprising a basic image capturing unit having an X-ray detecting panel and an extension device with a handle which is removably connected to the basic image capturing unit by a connector. The extension device has a battery circuit, a data recording means, and a wireless communication circuit.

The cassette disclosed in Japanese Laid-Open Patent Publication No. 2004-173907 includes electronic components such as the electric board, the image memory, etc., in addition to an X-ray detection array. The cassette disclosed in Japanese Patent No. 3494683 includes electronic components such as an image memory, a scanning pulse generator, and a transfer register in addition to a solid-state detector for detecting X-rays. The cassette disclosed in Japanese Laid-Open Patent Publication No. 2003-248060 includes electronic components such as a communication circuit and a power supply circuit in addition to the X-ray detection panel.

When X-ray images are recorded in the cassettes disclosed in Japanese Laid-Open Patent Publication No. 2004-173907, Japanese Patent No. 3494683, and Japanese Laid-Open Patent Publication No. 2003-248060, the electronic components thereof tend to be deteriorated or damaged by direct exposure to the X-rays.

For preventing the electronic components from being deteriorated or damaged, it is necessary to protect the electronic components against exposure to the X-rays with an X-ray shield such as a lead plate, for example. However, since the lead plate is heavy, it makes the cassette also heavy as a whole.

SUMMARY OF THE INVENTION

It is an object of the present invention to provide a cassette system which includes a cassette having a reduced weight and which has a reduced weight as a whole.

A cassette system according to the present invention comprises a cassette having radiation detector for detecting a radiation that has passed through a subject and converting the detected radiation into radiation image information, and a control unit for supplying electric power to the radiation detector and controlling the radiation detector to receive the radiation image information therefrom, the control unit being detachably mounted on and separable from the cassette.

Since the control unit which includes electronic components is separable from the cassette which includes the radiation detector, the amount of a radiation shield material used to shield the electronic components from the radiation is reduced, with the result that the cassette and the cassette system can be reduced in size and weight. Inasmuch as the cassette itself is small in size and weight, it can easily be placed below the subject, e.g., a patient, when the cassette is to be inserted between the subject and a bed for capturing the radiation image.

The control unit may comprise a battery for supplying the electric power and a wireless unit for sending the radiation image information to an external control device by way of wireless communications. When the radiation image is to be captured in the cassette, the control unit can easily be changed in attitude. A medium used for the wireless communications may be a radio wave sent and received by antennas, light emitted by LEDs or sound waves such as ultrasonic waves generated by ultrasonic transducers. If the radio wave sent and received by antennas is used, then the control unit may be changed in attitude to cause the directivity of the antenna on the control unit to match the directivity of the antenna on the external control device. As the transmission and reception sensitivity of the antennas for the radio wave is increased, the consumption of electric power stored in the battery is reduced.

The cassette and the control unit may be detachably connected to each other by a cable and at least one connector. Therefore, the cassette and the control unit can be handled with ease. If the connector is mounted on the cassette, then since the cassette is basically made up of the radiation detector, the connector, and a casing which houses them, the space in the casing is effectively utilized.

The cassette system may further comprise a take-up mechanism mounted on the control unit for winding up the cable such that the cable can be reeled out from the take-up mechanism. The cable may thus easily be accommodated in the control unit.

The control unit and/or the external control device may include a notifying unit for indicating electric field intensity information of the wireless communications. Using the notifying unit, the control unit can be placed in a location for higher electric field intensity.

The control unit or the cassette may include a detecting unit for detecting whether the control unit is separate from the cassette or not. When the radiation image is to be captured, it can be confirmed whether the control unit and the cassette are separate from each other or not, using the detecting unit.

According to the present invention, since the control unit including the electronic components is separable from the cassette including the radiation detector, the amount of an X-ray shield material used to shield the electronic components from the X-rays is reduced, with the result that the cassette and the cassette system can be reduced in size and weight.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 9 is a perspective view, partly cut away, of a cassette system according to another embodiment of the present invention;

DESCRIPTION OF THE PREFERRED EMBODIMENTS

Figure 1:
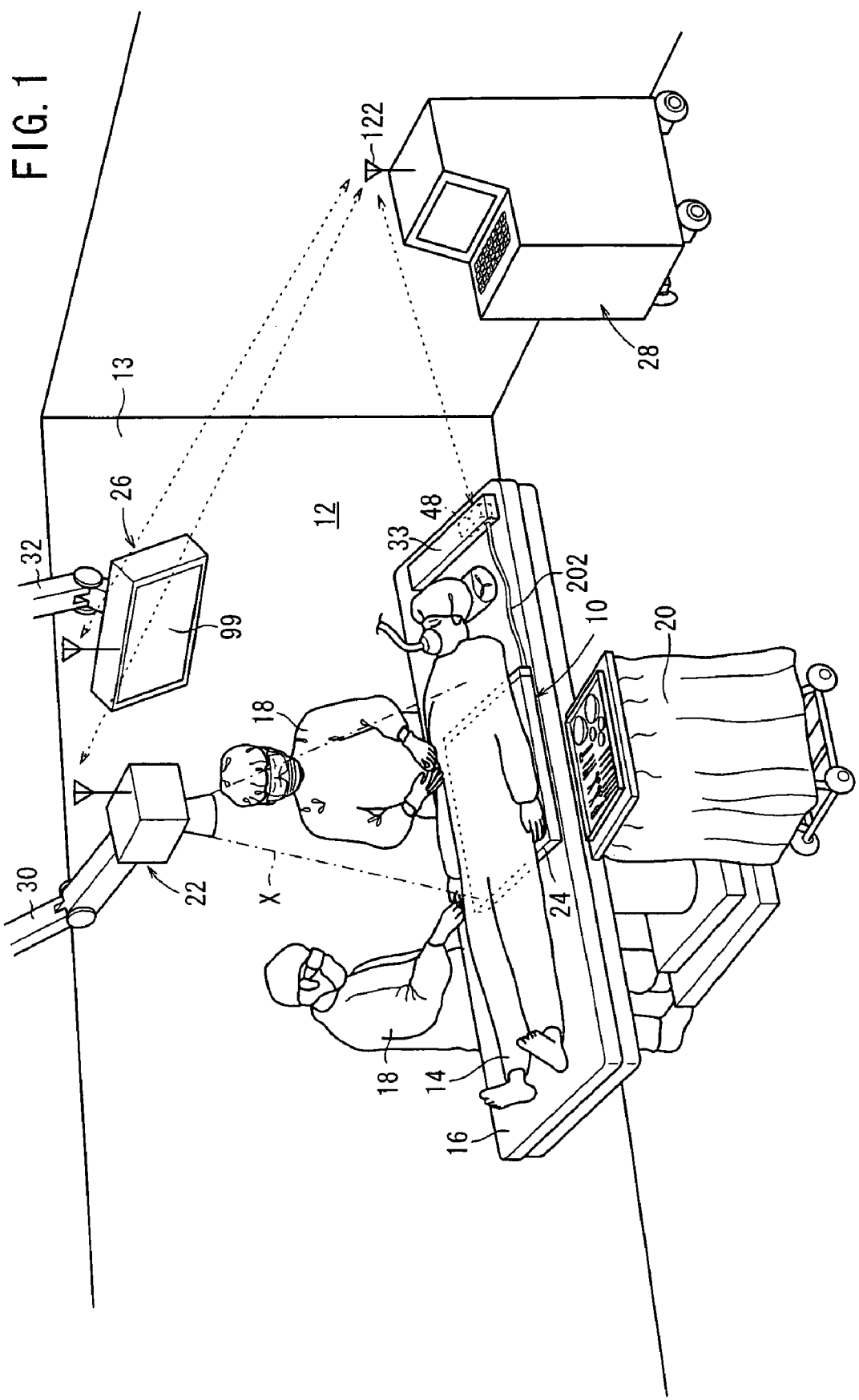
FIG. 1 is a perspective view of an operating room incorporating a radiation image capturing system which uses a cassette system according to an embodiment of the present invention.

Like or corresponding parts are denoted by like or corresponding reference characters throughout views.

Cassette systems according to preferred embodiments of the present invention, which are used in combination with radiation image capturing systems, will be described in detail below with reference to the accompanying drawings.

Figure 2:
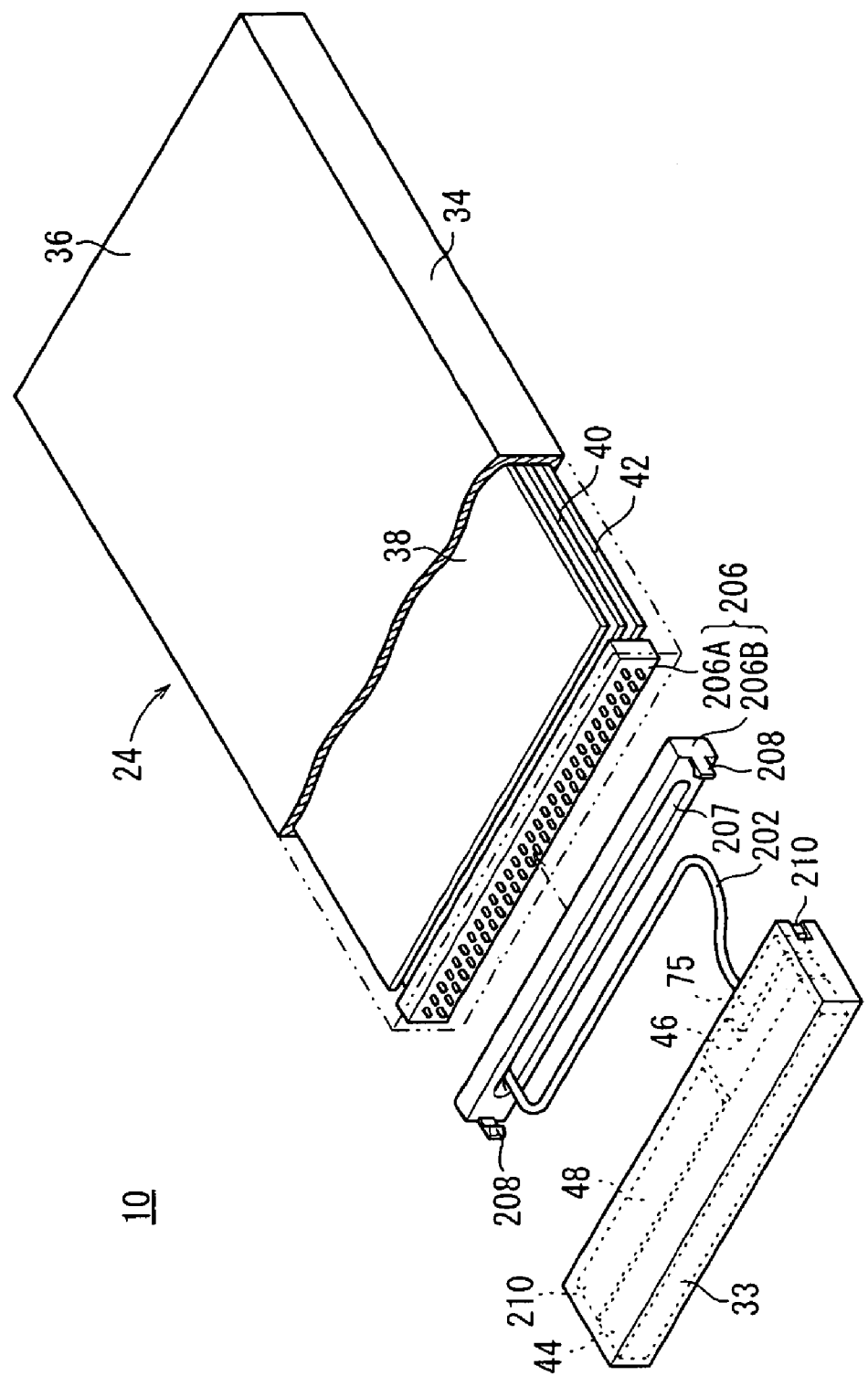
FIG. 2 is a perspective view, partly cut away, of the cassette system which has a control unit and a cassette that are disconnected from each other.

FIG. 1 shows in perspective an operating room 13 incorporating a radiation image capturing system 12 which employs a cassette system 10 according to an embodiment of the present invention. As shown in FIG. 2, the cassette system 10 comprises a cassette 24 and a control unit 33 connected to the cassette 24 by a cable 202.

The operating room 13 has, in addition to the radiation image capturing system 12 which employs the cassette system 10, a surgical table 16 for a patient 14 to lie thereon, and an instrument table 20 disposed to one side of the surgical table 16 for placing thereon various tools and instruments to be used by surgeons 18 operating on the patient 14. The surgical table 16 is surrounded by various apparatus required for surgical operations, including an anesthesia apparatus, an aspirator, an electrocardiograph, a blood pressure monitor, etc.

The radiation image capturing system 12 includes an image capturing apparatus 22 for irradiating the patient 14 with a radiation X at a dose according to image capturing conditions, the cassette system 10 including the cassette (radiation detecting cassette) 24 which houses therein a radiation detector, to be described later, for detecting the radiation X that has passed through the patient 14, a display device 26 for displaying a radiation image based on the radiation X that is detected by the radiation detector, and a console (external control device) 28, which serves as an image processor, for controlling the image capturing apparatus 22, the cassette 24, and the display device 26.

The console 28, the image capturing apparatus 22, the control unit 33, and the display device 26 send and receive signals by way of wireless communications as indicated by the broken lines. In FIG. 1, radio waves are used to send and receive signals between the console 28, the image capturing apparatus 22, the control unit 33, and the display device 26. However, the medium used for wireless communications is not limited to radio waves, but may be light emitted by LEDs or sound waves such as ultrasonic waves generated by ultrasonic transducers.

The image capturing apparatus 22 is coupled to a universal arm 30 so as to be movable to a desired position for capturing an image at a desired area of the patient 14 and also to be retractable to an out-of-the-way position while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 3:
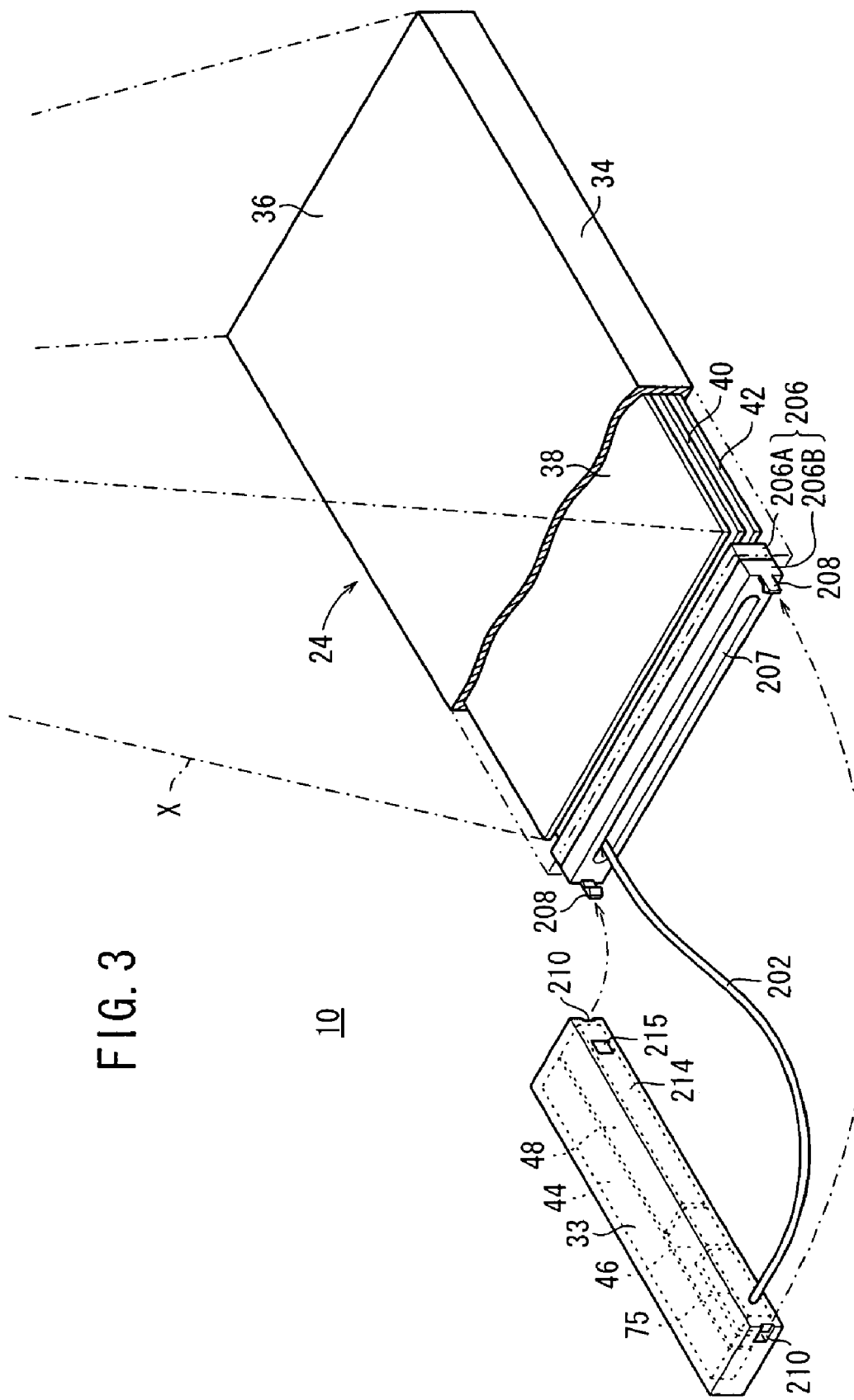
FIG. 3 is a perspective view, partly cut away, of the cassette system which has the control unit and the cassette that are connected to each other at the time an image is captured in the cassette.

FIGS. 2 and 3 shows in perspective, partly cut away, the cassette system 10 according to the present embodiment. As described above, the cassette system 10 comprises the cassette 24 and the control unit 33. The cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays from the radiation X. The grid 38, the radiation detector 40 and the lead plate 42 are successively arranged in that order from an irradiated surface 36 of the casing 34 which is irradiated with the radiation X. The irradiated surface 36 of the casing 34 may be constructed as the grid 38. A connector (male connector) 206A is mounted on a longitudinal end face of the casing 34. Therefore, since the cassette 24 essentially includes a radiation detection assembly having the radiation detector 40, the connector 206A, and the casing 34, the cassette 24 is relatively small in size and weight. The casing 34 has an internal space that is effectively utilized.

As shown in FIG. 3, the connector 206A is connected to a connector (female connector) 206B that is connected to the control unit 33 by a cable 202. The connector 206A and the connector 206B jointly make up a connector assembly 206.

The control unit 33 comprises a battery 44 as a power supply of the cassette 24, a cassette controller 46 for energizing the radiation detector 40 with electric power supplied from the battery 44, an interface circuit 75 disposed between the cassette controller 46 and the cable 202, and a communication unit 48 as a wireless unit with an antenna incorporated therein. The battery 44 may be separate from the control unit 33.

The cable 202 has an end connected to the interface circuit 75 and the other end connected to the connector 206B. The cable 202 can be stored in a storage space (cavity) 207 defined in a rear surface of the connector 206B.

Figure 4:
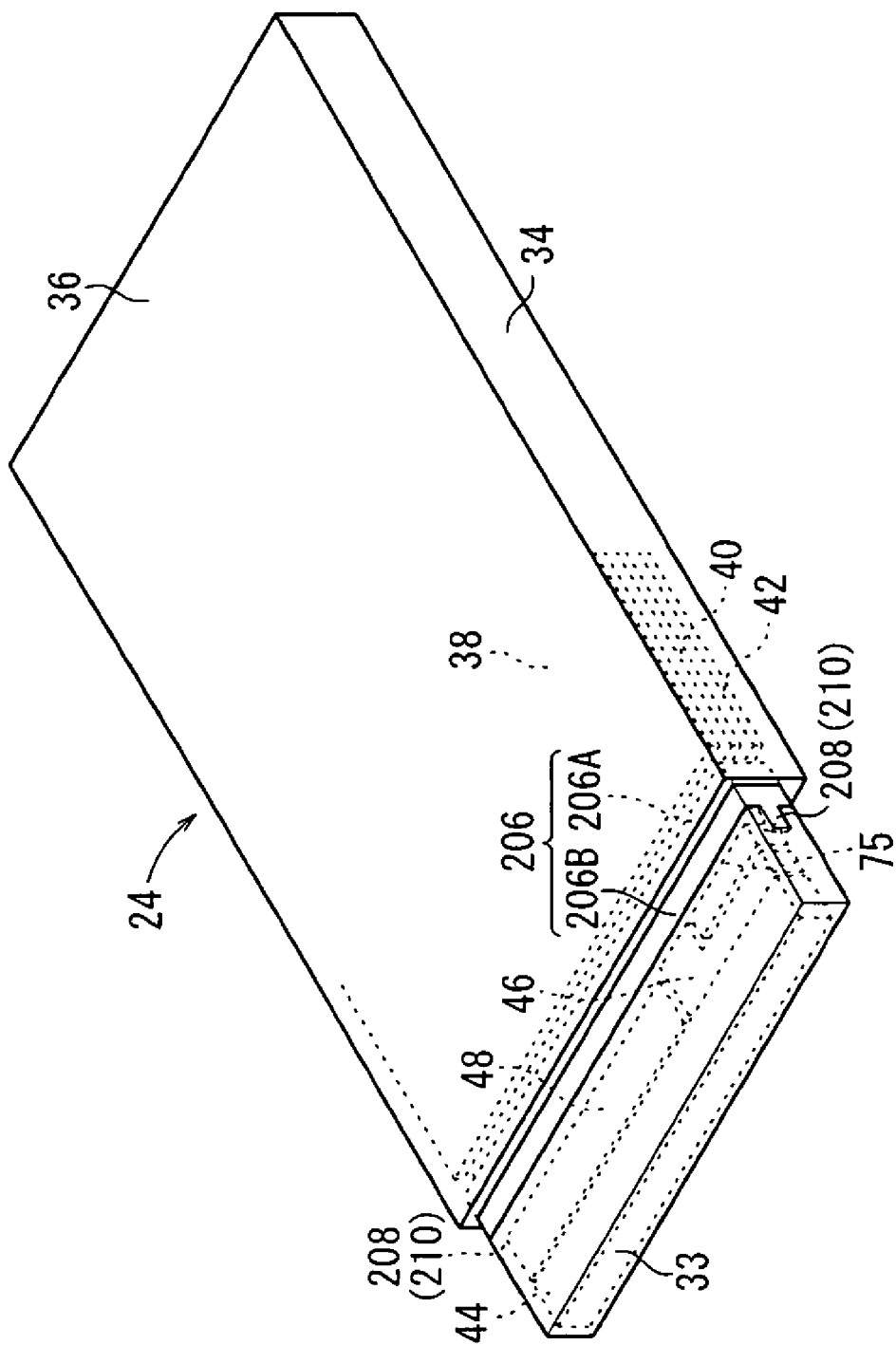
FIG. 4 is a perspective view of the cassette system which has the control unit and the cassette that are integrally connected to each other.

As shown in FIG. 3, the connector 206B connected to the control unit 33 is connected to (fitted over) the connector 206A of the cassette 24. At this time, the control unit 33 is separate from, but connected by the cable 202 to, the connector 206B. Then, as shown in FIG. 4, the cable 202 is stored in the storage space 207 (see FIGS. 2 and 3), and fingers (engaging members) 208 mounted on respective longitudinal ends of the connector 206B engage in respective recesses (engaging members) 210 defined in respective longitudinal ends of the control unit 33, thereby locking the control unit 33 on the cassette 24. In this manner, the cassette system 10 is integrated.

Figure 5:
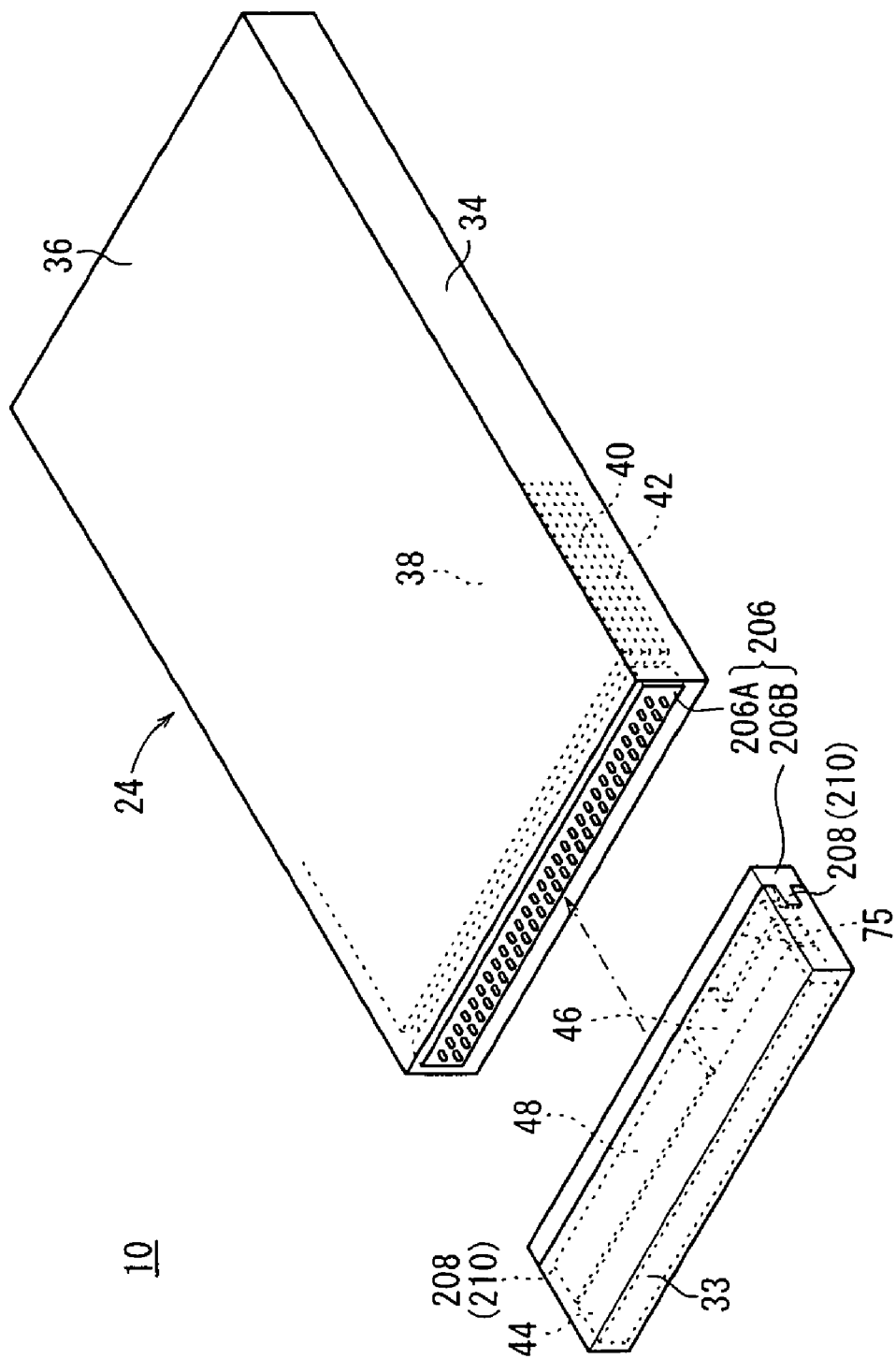
FIG. 5 is a perspective view of the cassette system in the state where the control unit is removed from the cassette.

The cassette system 10 as it configured as shown in FIG. 3 is in an image capturing mode. The cassette system 10 as it configured as shown in FIG. 4 is in a portable mode or a storage mode. The cassette 24 and the control unit 33 may be disconnected from each other as shown in FIG. 5. The cassette system 10 as it configured as shown in FIG. 5 is also in the portable mode or the storage mode. In FIG. 2, the connector 206B is removed from, but remains connected to, the control unit 33, though the connectors 206A, 206B are disconnected from each other. When the cassette system 10 is configured as shown in FIG. 5, the control unit 33 may be connected to a battery charger, not shown, to charge the battery 44.

The communication unit 48 sends and receives signals including the information of the radiation X detected by the radiation detector 40, i.e., signals acquired from the radiation detector 40 through the connector assembly 206 (206A, 206B), the cable 202, and the interface circuit 75, to and from the console 28 which serves as an external control device.

The communication unit 48 includes a circuit board having an antenna 212, to be described later, printed thereon.

Therefore, the directivity of the antenna 212 can easily be changed when the orientation of the control unit 33 is changed.

Figure 6:
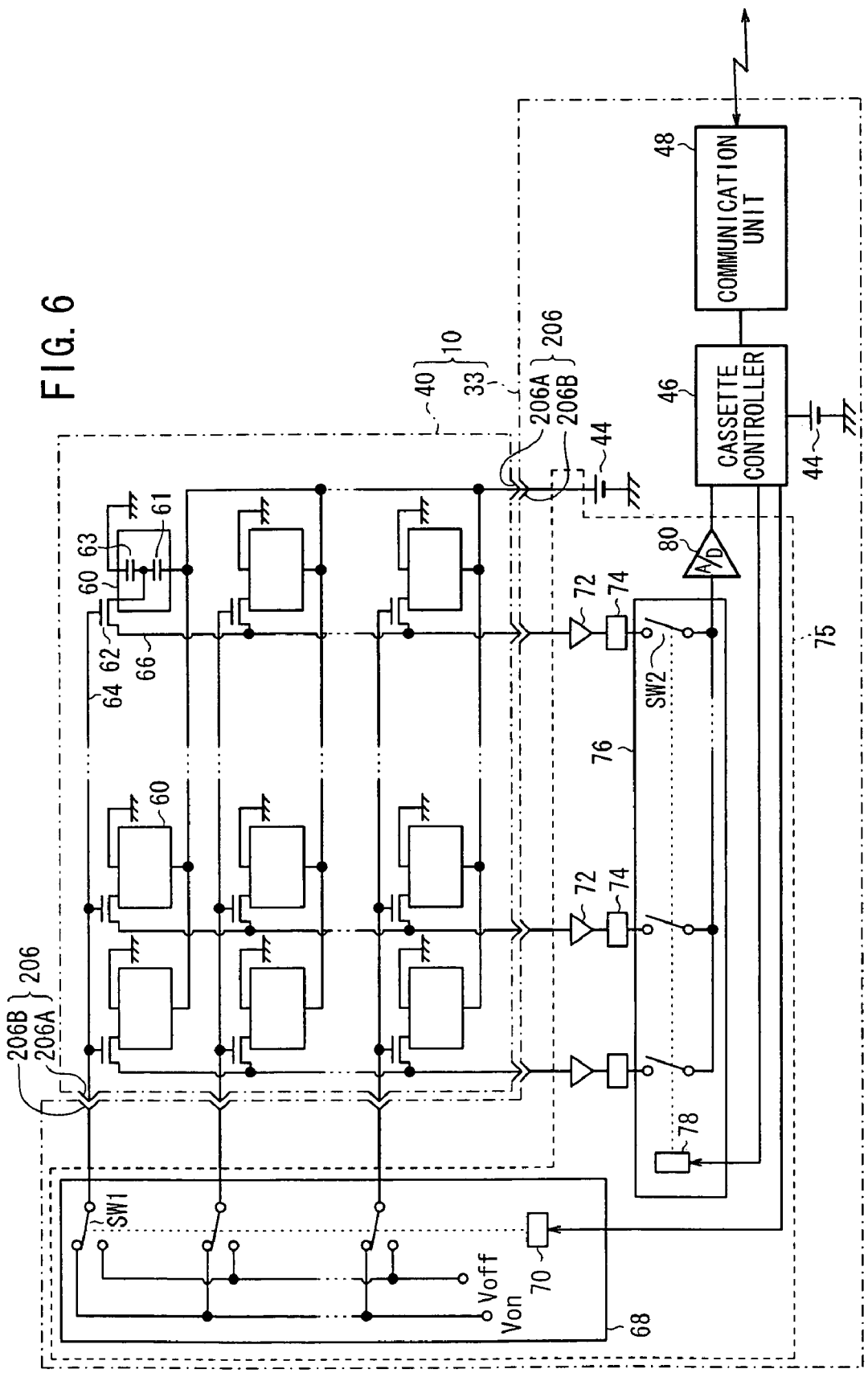
FIG. 6 is a block diagram of a circuit arrangement of the cassette system.

FIG. 6 shows in block form a circuit arrangement of the cassette system 10 including the radiation detector 40 and the control unit 33.

As shown in FIG. 6, the radiation detector 40 comprises an array of thin-film transistors (TFTs) 62 arranged in rows and columns, a photoelectric conversion layer 61 made of a material such as amorphous selenium (a-Se) for generating electric charges upon detection of the radiation X, the photoelectric conversion layer 61 being disposed over the array of TFTs 62, and an array of storage capacitors 63 connected to the photoelectric conversion layer 61. When the radiation X is applied to the radiation detector 40, the photoelectric conversion layer 61 generates electric charges, and the storage capacitors 63 store the generated electric charges. Then, the TFTs 62 are turned on along each row at a time to read out the electric charges from the storage capacitors 63 as an image signal. In FIG. 6, the photoelectric conversion layer 61 and one of the storage capacitors 63 are shown as a pixel 60, and the pixel 60 is connected to one of the TFTs 62. Details of the other pixels 60 are omitted from illustration. Since amorphous selenium tends to change its structure and lose its functionality at high temperatures, it needs to be used within a certain temperature range. Therefore, some means for cooling the radiation detector 40 should preferably be provided in the cassette 24.

The TFTs 62 connected to the respective pixels 60 are connected to respective gate lines 64 extending parallel to the rows and respective signal lines 66 extending parallel to the columns. The gate lines 64 are connected to a line scanning driver 68 in the interface circuit 75 by the connector assembly 206 (206A, 206B), and the signal lines 66 are connected to a multiplexer 76 serving as a reading circuit in the interface circuit 75 by the connector assembly 206 (206A, 206B).

The gate lines 64 are supplied with control signals Von, Voff for turning on and off the TFTs 62 along the rows from the line scanning driver 68. The line scanning driver 68 comprises a plurality of switches SW1 for switching between the gate lines 64, and an address decoder 70 for outputting a selection signal for selecting one of the switches SW1 at a time. The address decoder 70 is supplied with an address signal from the cassette controller 46 via the interface circuit 75.

The signal lines 66 are supplied with electric charges stored in the storage capacitors 63 of the pixels 60 through the TFTs 62 arranged in the columns. The electric charges supplied to the signal lines 66 are amplified by amplifiers 72 of the interface circuit 75 which are connected respectively to the signal lines 66. The amplifiers 72 are connected through respective sample and hold circuits 74 to the multiplexer 76. The multiplexer 76 comprises a plurality of switches SW2 for switching between the signal lines 66, and an address decoder 78 for outputting a selection signal for selecting one of the switches SW2 at a time. The address decoder 78 is supplied with an address signal from the cassette controller 46. The multiplexer 76 has an output terminal connected to an A/D converter 80. A radiation image signal generated by the multiplexer 76 based on the electric charges from the sample and hold circuits 74 is converted by the A/D converter 80 into a digital image signal representing radiation image information, which is supplied to the cassette controller 46 via the interface circuit 75. The cassette controller 46 is connected to the communication unit 48.

Figure 7:
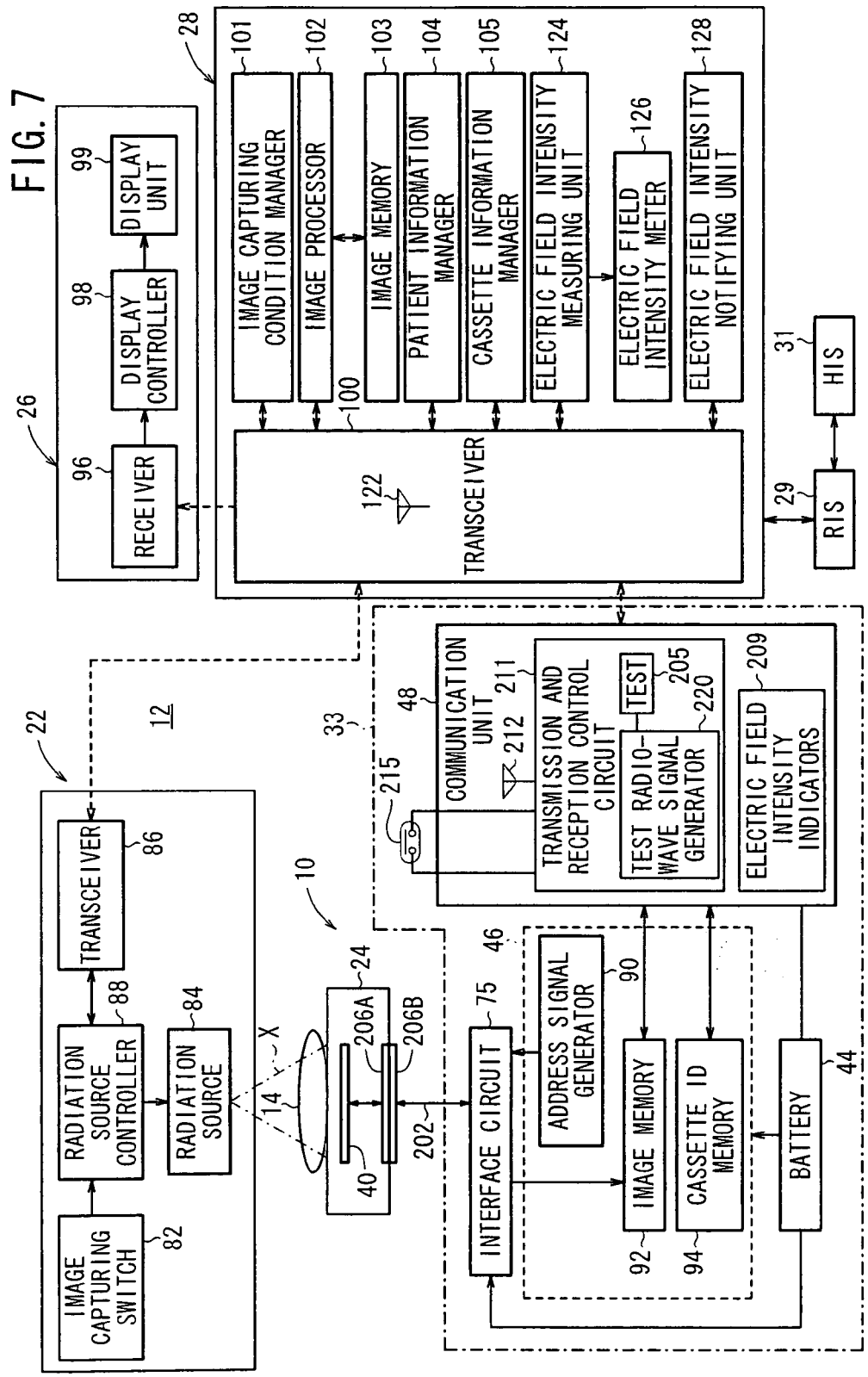
FIG. 7 is a block diagram of the radiation image capturing system shown in FIG. 1.

FIG. 7 shows in block form the radiation image capturing system 12 which comprises the image capturing apparatus 22, the cassette system 10 made up of the cassette 24 and the control unit 33, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 82, a radiation source 84 for outputting the radiation X, a transceiver 86 for receiving image capturing conditions from the console 28 by way of wireless communications and transmitting an image capturing completion signal, etc. to the console 28 by way of wireless communications, and a radiation source controller 88 for controlling the radiation source 84 based on an image capturing start signal supplied from the image capturing switch 82 and image capturing conditions supplied from the transceiver 86.

The cassette 24 houses therein the radiation detector 40 and the connector 206A.

The control unit 33 houses therein the battery 44, the cassette controller 46, the communication unit 48, and the interface circuit 75.

The cassette controller 46 comprises an address signal generator 90 for supplying address signals to the address decoder 70 of the line scanning driver 68 and the address decoder 78 of the multiplexer 76 of the interface circuit 75, an image memory 92 for storing the radiation image information detected by the radiation detector 40, and a cassette ID memory 94 for storing cassette ID information for identifying the cassette 24.

The communication unit 48 includes a transmission and reception control circuit 211. With the communication unit 48 being electrically connected to the cassette controller 46, the transmission and reception control circuit 211 receives a transmission request signal from the console 28 by way of wireless communications and transmits the cassette ID information stored in the cassette ID memory 94 and the radiation image information stored in the image memory 92 to the console 28 by way of wireless communications. The communication unit 48 also has electric field intensity indicators 209. The transmission and reception control circuit 211 has a test radio-wave signal generator 220 and a test switch button 205. A proximity switch 215 is connected to the communication unit 48.

The interface circuit 75, the cassette controller 46, the communication unit 48, and the radiation detector 40 connected to the interface circuit 75 of the control unit 33 are supplied with electric power from the battery 44. If the radiation detector 40 needs a high voltage, then the interface circuit 75 may include a high-voltage generating circuit, and a high voltage generated by the high-voltage generating circuit may be applied as a bias to the radiation detector 40.

The display device 26 comprises a receiver 96 for receiving radiation image information from the console 28, a display controller 98 for controlling the display of the received radiation image information, and a display unit 99 for displaying the radiation image information processed by the display controller 98.

The console 28 comprises a transceiver 100 for transmitting and receiving necessary information including radiation image information to and from the image capturing apparatus 22, the control unit 33 of the cassette system 10, and the display device 26 by way of wireless communications through an antenna 122 (see also FIG. 1), an image capturing condition manager 101 for managing image capturing conditions required for the image capturing apparatus 22 to capture radiation images, an image processor (image processing means) 102 for processing radiation image information transmitted from the cassette 24, an image memory 103 for storing the radiation image information processed by the image processor 102, a patient information manager 104 for managing patient information of the patient 14 whose images are to be captured, a cassette information manager (managing means) 105 for managing cassette information including an accumulated exposed dosage transmitted from the cassette 24, an electric field intensity measuring unit 124, an electric field intensity meter 126, and an electric field intensity notifying unit 128.

The console 28 may be located outside of the operating room 13 insofar as it can transmit and receive signals to and from the image capturing apparatus 22, the control unit 33, and the display device 26 by way of wireless communications.

The image capturing conditions refer to conditions for determining a tube voltage, a tube current, an irradiation time, etc. required to apply a radiation X at an appropriate dose to an area of the patient 14 to be imaged. The image capturing conditions may include an area of the patient 14 to be imaged, an image capturing method, etc., for example. The patient information refers to information for identifying the patient 14, such as the name, gender, patient ID number, etc. of the patient 14. Ordering information to capture an image, including the image capturing conditions and the patient information, can be set directly on the console 28 or can be supplied from an external source to the console 28 via the RIS 29. The cassette information refers to, for example, cassette ID information for identifying the cassette 24.

The radiation image capturing system 12 which employs the cassette system 10 according to the present embodiment is basically constructed as described above, and operation of the radiation image capturing system 12 will be described below.

The radiation image capturing system 12 is installed in the operating room 13 and used when a radiation image of the patient 14 is required by the surgeons 18 who are performing an operation on the patient 14. Before a radiation image of the patient 14 is captured, patient information of the patient 14 to be imaged is registered in the patient information manager 104 of the console 28. If an area of the patient 14 to be imaged and an image capturing method have already been known, such information is registered as image capturing conditions in the image capturing condition manager 101. After the above preparatory process is completed, the surgeons 18 perform an operation on the patient 14.

For capturing a radiation image of the patient 14 during the operation, one of the surgeons 18 or the radiological technician in charge places the cassette 24 in a given position between the patient 14 and the surgical table 16 with the irradiated surface 36 facing the image capturing apparatus 22. Since the cassette 24 itself is relatively small in size and weight, it can easily be placed between the patient 14 and the surgical table 16.

As shown in FIG. 1, one of the surgeons 18 or the radiological technician places the control unit 33 which includes the communication unit 48, which is connected to the cassette 24 by the cable 202, in an appropriate position on the surgical table 16 remotely from the cassette 24 in the configuration shown in FIG. 3.

At this time, the transmission and reception control circuit 211 of the communication unit 48 supplies a test radio-wave signal from the test radio-wave signal generator 220 to the antenna 212, which radiates a test radio wave. The surgeon 18 or the radiological technician determines the orientation and position of the communication unit 48, i.e., the position of the antenna 212 of the control unit 33, such that the reception intensity of the radio wave that is sent from the antenna 212 and received by the transceiver 100 of the console 28 via the antenna 122 thereof will be maximized.

Specifically, the surgeon 18 or the radiological technician positions the control unit 33 so as to maximize the electric field intensity while watching the pointer of the electric field intensity meter 126 or the indications given by the electric field intensity indicators 209.

Then, after having moved the image capturing apparatus 22 to a position confronting the cassette 24, one of the surgeons 18 or the radiological technician operates the image capturing switch 82 to capture a radiation image of the patient 14.

As shown in FIG. 3, the proximity switch 215 is disposed on a surface 214 of the control unit 33 which faces the connector 206B. Alternatively, the proximity switch 215 may be mounted on the connector 206B. When the image capturing switch 82 is operated, if the proximity switch 215 is not turned off, i.e., if the control unit 33 is not removed from, but is mounted on, the connector 206B and hence the proximity switch 215 is turned on, then the on-state of the proximity switch 215 is detected by the communication unit 48 of the control unit 33.

When the on-state of the proximity switch 215 is detected by the communication unit 48, the transmission and reception control circuit 211 indicates the on-state of the proximity switch 215 to the radiation source controller 88 of the image capturing apparatus 22 via the transceiver 100 of the console 28 and/or to the image capturing condition manager 101 of the console 28.

Therefore, when the image capturing switch 82 is turned on, the radiation source controller 88 issues a warning "REMOVE CONTROL UNIT FROM CASSETTE. RADIATION CAPTURING SWITCH CANNOT BE TURNED ON (CLOSED) TO APPLY RADIATION." from a speaker, not shown, of the image capturing apparatus 22. In this manner, if the control unit 33 is not separated from the connector 206B (the cassette 24) as detected by the proximity switch 215 on the control unit 33, then the action on the image capturing switch 82 to turn it on is invalidated.

Consequently, the proximity switch 215 functions as a means (separation detecting unit) for detecting whether the control unit 33 is separated from the connector 206B (the cassette 24) or not.

If the proximity switch 215 is turned off and the control unit 33 is separated from the connector 206B (the cassette 24), then the on-state of the proximity switch 215 is indicated to the radiation source controller 88 and/or to the image capturing condition manager 101.

In this case, when the image capturing switch 82 is turned on, the radiation source controller 88 of the image capturing apparatus 22 acquires the image capturing conditions for an area of the patient 14 to be imaged from the image capturing condition manager 101 of the console 28 via the transceivers 100, 86. The radiation source controller 88 then controls the radiation source 84 to apply a radiation X at a given dose to the patient 14 according to the acquired image capturing conditions.

The radiation X which has passed through the patient 14 is applied to the grid 38, which removes scattered rays from the radiation X. Then, the radiation X is applied to the radiation detector 40, and converted into electric signals by the photoelectric conversion layer 61 of the pixels 60 of the radiation detector 40. The electric signals are stored as electric charges in the storage capacitors 63. The stored electric charges, which represent radiation image information of the patient 14, are read out from the storage capacitors 63 according to address signals which are supplied from the address signal generator 90 of the cassette controller 46 to the line scanning driver 68 and the multiplexer 76.

Specifically, in response to the address signal supplied from the address signal generator 90, the address decoder 70 of the line scanning driver 68 outputs a selection signal to select one of the switches SW1, which supplies the control signal Von to the gates of the TFTs 62 connected to the gate line 64 corresponding to the selected switch SW1. In response to the address signal supplied from the address signal generator 90, the address decoder 78 of the multiplexer 76 outputs a selection signal to successively turn on the switches SW2 to switch between the signal lines 66 for thereby reading out the electric charges stored in the storage capacitors 63 of the pixels 60 connected to the selected gate line 64, through the signal lines 66, to obtain the radiation image information.

The electric charges read out from the storage capacitors 63 of the pixels 60 connected to the selected gate line 64 are amplified by the respective amplifiers 72, sampled by the sample and hold circuits 74, and supplied to the multiplexer 76. Based on the supplied electric charges, the multiplexer 76 generates and supplies a radiation image signal to the A/D converter 80, which converts the radiation image signal into a digital signal. The digital signal which represents the radiation image information is temporally stored in the image memory 92 of the cassette controller 46.

Similarly, the address decoder 70 of the line scanning driver 68 successively turns on the switches SW1 to switch between the gate lines 64 according to the address signal supplied from the address signal generator 90. The electric charges stored in the storage capacitors 63 of the pixels 60 connected to the successively selected gate lines 64 are read through the signal lines 66, and processed by the multiplexer 76 and the A/D converter 80 into digital signals which represent the radiation image information are stored in the image memory 92 of the cassette controller 46.

The radiation image information stored in the image memory 92 is read from the image memory 92 and transmitted to the console 28 by way of wireless communications via the antenna 212 of the communication unit 48. The radiation image information transmitted to the console 28 is received by the transceiver 100, processed by the image processor 102, and then stored in the image memory 103 in association with the patient information of the patient 14 registered in the patient information manager 104.

The processed radiation image information is transmitted from the transceiver 100 to the display device 26 where it is received by the receiver 96. In the display device 26, the display controller 98 controls the display unit 99 to display a radiation image based on the radiation image information. The surgeons 18 perform the operation on the patient 14 while confirming the radiation image displayed on the display unit 99.

Since no cables for transmitting and receiving signals are connected between the control unit 33 of the cassette 24 and the console 28, between the image capturing apparatus 22 and the console 28, and between the console 28 and the display device 26, it is not necessary to lay cables on the floor of the operating room 13. Therefore, a tidy working environment is established in the operating room 13 to allow the surgeons 18 to work efficiently and smoothly without being hampered by obstacles such as cables.

According to a cassette of the related art which is designed to accommodate an antenna therein, it may be difficult for the cassette to have an antenna of such specifications for the frequency and wavelength used for desired wireless communications in relation to the layout of the battery and other components in the cassette. With the cassette system 10 according to the present embodiment, the antenna 212 is accommodated in the communication unit 48 of the control unit 33, and the communication unit 48 is electrically connected to the cassette 24 by the cable 202. Accordingly, the antenna 212 may be of a configuration suitable for the frequency and wavelength used for desired wireless communications. As a result, the communication unit 48 of the control unit 33 and the console 28 can achieve stable communications therebetween and hence the display device 26 can display high-quality radiation images.

As described above, the cassette system 10 according to the present embodiment includes the cassette 24 having the radiation detector 40 for detecting the radiation X that has passed through the subject, i.e., the patient 14, and converting the detected radiation X into radiation image information, and the control unit 33 which is detachably mounted on and separable from the cassette 24. When the control unit 33 is mounted on the cassette 24, the control unit 33 supplies electric power from the battery 44 to the radiation detector 40 and controls the radiation detector 40 to receive the radiation image information therefrom.

According to the cassette system 10, since the control unit 33 including electronic components such as the interface circuit 75, the cassette controller 46, and the communication unit 48 is separable from the cassette 24 including the radiation detector 40, the amount of a radiation shield material such as a lead plate or the like used to shield the electronic components from the radiation is reduced, with the result that the cassette 24 and hence the cassette system 10 can be reduced in size and weight.

The control unit 33 that is connected to the cassette 24 by the cable 202 includes the battery 44 and the communication unit 48 for sending the image information to the external control device via the antenna 212. When the control unit 33 is changed in attitude while radiation image information is being captured in the cassette 24, the antenna 212 can easily be changed in attitude. Therefore, it is easy to match the directivity of the antenna 212 of the communication unit 48 and the directivity of the antenna 122 of the console 28, so that the communication unit 48 and the console 28 can perform wireless communications highly efficiently and the power consumption of the battery 44 can be reduced.

As the cassette 24 and the control unit 33 are detachably connected to each other by the cable 202 and at least one connector assembly 206 (206A, 206B), they can be handled with ease. While radiation image information is being captured in the cassette 24, any damage to the control unit 33 due to the exposure to the radiation X is minimized because the control unit 33 is spaced from the cassette 24.

The process of positioning the control unit 33 at a location for achieving the greatest electric field intensity while watching the pointer of the electric field intensity meter 126 or the indications given by the electric field intensity indicators 209 will be described in further detail below. The console 28 includes the electric field intensity measuring unit (electric field intensity measuring and determining unit) 124, the electric field intensity meter 126 such as a VU meter or the like, and the electric field intensity notifying unit 128. The communication unit 48 of the control unit 33 includes the test radio-wave signal generator 220, the test switch button 205, and the electric field intensity indicators 209.

Figure 8A:
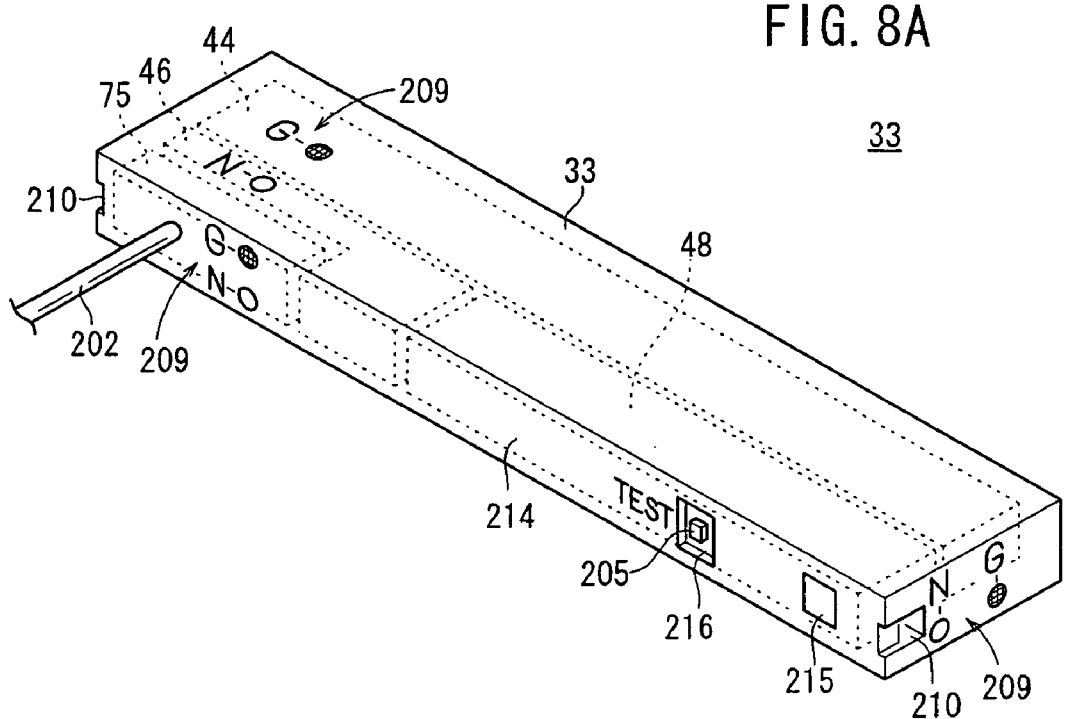
FIG. 8A is a perspective view of a control unit with an electric field intensity information notifying unit.

As shown in FIG. 8A, the electric field intensity indicators (electric field intensity information notifying unit) 209 of the control unit 33 are mounted respectively on all the six outer surfaces of the control unit 33 which is in the shape of a rectangular parallelepiped. Each of the electric field intensity indicators 209 comprises a green LED (Light-Emitting Diode) associated with the letter "G" and a red LED associated with the letter "N". When the electric field intensity measured by the electric field intensity measuring unit 124 is acceptable, i.e., is equal to or greater than a predetermined level, the green LEDs on all the electric field intensity indicators 209 are simultaneously turned on. When the electric field intensity measured by the electric field intensity measuring unit 124 is not acceptable, i.e., is lower than the predetermined level, the red LEDs on all the electric field intensity indicators 209 are simultaneously turned on.

The control unit 33 includes a surface 214, which is one of the six outer surfaces of the control unit 33 that faces the cassette 24 (the connector 206B), having a recess 216 (see FIG. 8A) defined therein. The recess 216 houses therein the test switch button 205 which is connected to the test radio-wave signal generator 220.

The radiation image capturing system 12 shown in FIG. 7 operates as follows: When one of the surgeons 18 or the radiological technician removes the control unit 33 from the connector 206B, spaces the cassette 24 and the control unit 33 from each other, but keeps them interconnected by the cable 202, and positions the control unit 33 (the communication unit 48) on the surgical table 16 as shown in FIG. 1 before capturing a radiation image of the patient 14, the surgeon 18 or the radiological technician presses the test switch button 205. The test radio-wave signal generator 220 is turned on to send a test radio wave from the transmission and reception control circuit 211 of the communication unit 48 via the antenna 212.

The radiated test radio wave is received by the transceiver 100 of the console 28 via the antenna 122 thereof. The electric field intensity measuring unit 124 measures the electric field intensity of the received test radio wave and determines whether the electric field intensity of the measured test radio wave is equal to or greater than a predetermined electric field intensity for smooth wireless communications or not.

The determined result is transmitted from the electric field intensity notifying unit 128 of the console 28 to the communication unit 48 via the transceiver 100 and the antenna 122.

Based on the received determined result, the communication unit 48 turns on the green LEDs or the red LEDs of the electric field intensity indicators 209. In FIG. 8A, the green LEDs are shown as being turned on, indicating that the electric field intensity of the measured test radio wave is acceptable.

Figure 8B:
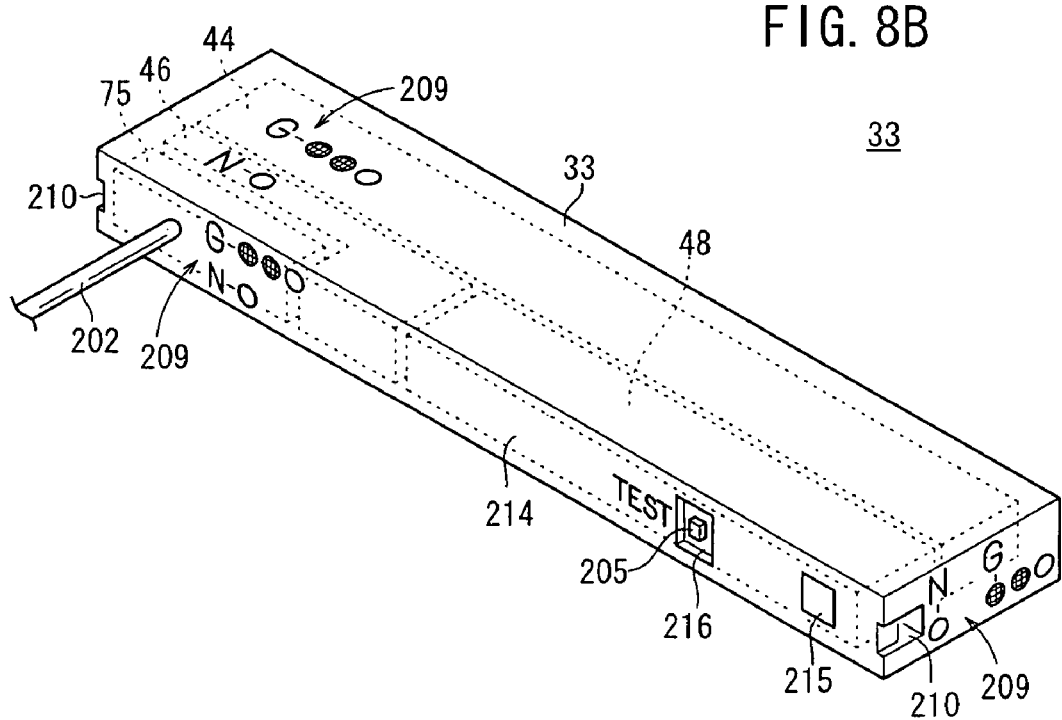
FIG. 8B is a perspective view of another control unit with an electric field intensity notifying unit.

The electric field intensity indicators 209 may produce a stepped or stepless indication depending on the electric field intensity of the measured test radio wave when it is acceptable. In FIG. 8B, each of the electric field intensity indicators 209 comprises three green LEDs, and two of the green LEDs are shown as being turned on. When all the three green LEDs shown in FIG. 8B are turned on, they indicate that the electric field intensity of the measured test radio wave is of the greatest level. The surgeon 18 or the radiological technician may change the position of the communication unit 48 to place the communication unit 48 in a location where a largest number of green LEDs of the electric field intensity indicators 209 are turned on.

The determined electric field intensity may be indicated to the surgeons 18 and the radiological technician by a speech signal and/or may be displayed on the display unit 99 of the display device 26.

The electric field intensity of the test radio wave measured by the electric field intensity measuring unit 124 is also displayed by the electric field intensity meter (electric field intensity information notifying unit) 126 of the console 28. The control 28 may also display the determined electric field intensity on itself. When positioning the communication unit 48, the surgeon 18 or the radiological technician can place the control unit 33 (the communication unit 48) in a position where the electric field intensity is maximum by seeing the electric field intensity displayed by the electric field intensity meter 126. The test radio wave may be generated in the console 28 rather than in the communication unit 48.

The present invention is not limited to the illustrated embodiments. However, changes and modifications may be made to the embodiments without departing from the scope of the invention.

For example, as shown in FIG. 9, the connector 206B of the control unit 33 may have a take-up mechanism 200 for winding up a flexible cable 202. The take-up mechanism 200 stores therein the cable 202 as a wound roll so that the cable 202 can be reeled out to a desired length under the tension of a tension spring acting thereon. The take-up mechanism 200 can thus easily store the cable 202 therein. The take-up mechanism 200 may be incorporated in the main body of the control unit 33 which includes the cassette controller 46.

According to the illustrated embodiments, the radiation image capturing system 12 is used while an operation is being performed on the patient 14 to display radiation image information of the patient 14 on the display device 26. However, the radiation image capturing system 12 is also applicable to capture other radiation images than those captured in surgical operations.

In the radiation image capturing systems according to the embodiments, the radiation detector 40 housed in the cassette 24 directly converts the dose of the applied radiation X into an electric signal with the photoelectric conversion layer 61. However, the radiation image capturing systems may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing systems may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

Signals may be transmitted and received between the image capturing apparatus 22, the display device 26, and the console 28 by way of wired communications.

When the cassette system 10 is used in the operating room 13 or the like, blood stains and contaminants may be applied to the cassette system 10. The cassette system 10 may be of a water-resistant, sealed structure so that it can be sterilized and cleaned to remove such blood stains and contaminants for repetitive use.

The cassette system 10 is not limited to being used in the operating room 13, but may be used in combination with medical examinations and doctor's visits to patient rooms in the hospital.

The cassette system 10 and the console 28 as an external device may communicate with each other by way of optical wireless communications using infrared rays or the like, rather than usual wireless communications using radio waves.

Figure 10:
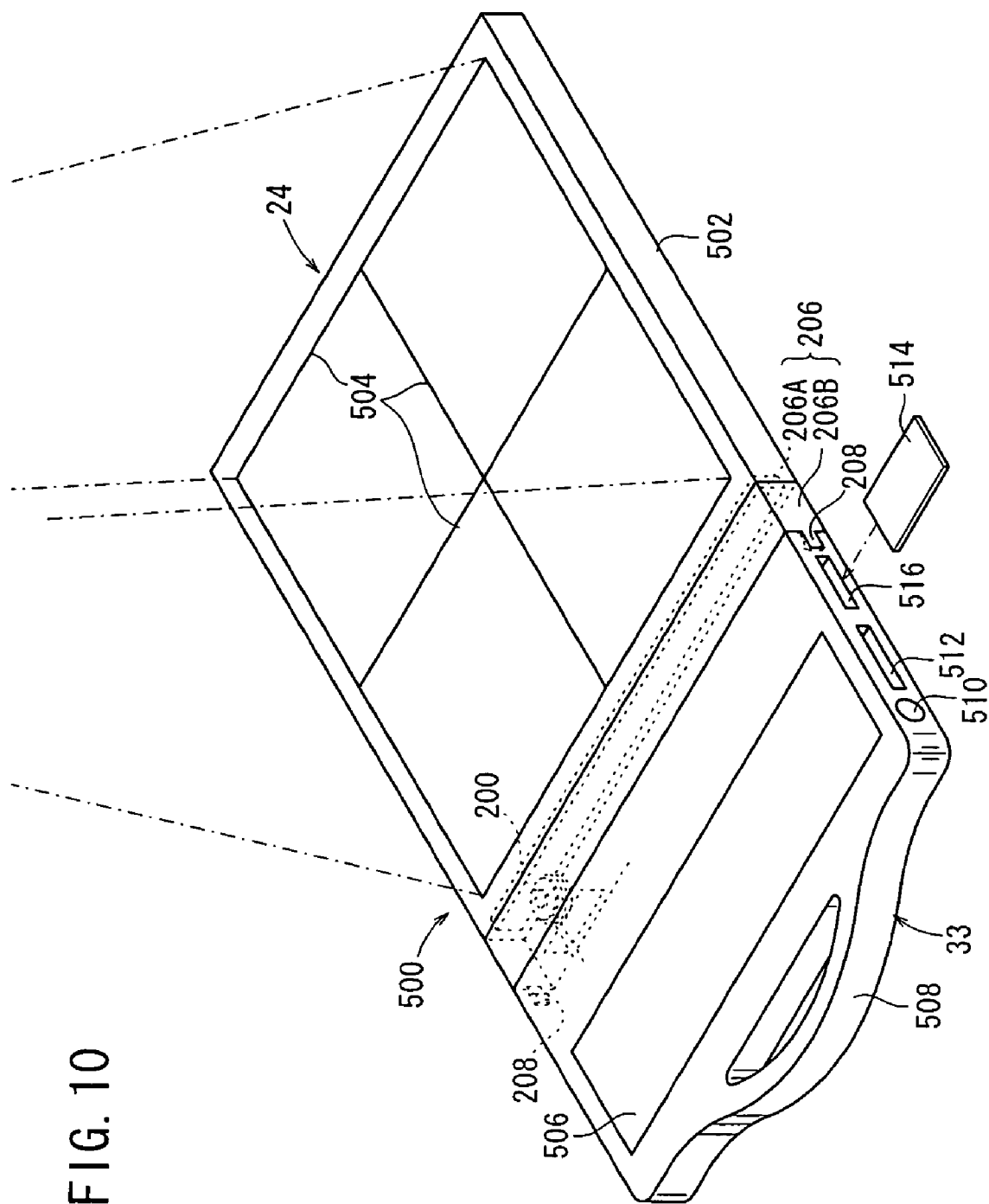
FIG. 10 is a perspective view of a cassette system according to still another embodiment of the present invention.

FIG. 10 shows in perspective a cassette system 500 according to another embodiment of the present invention.

As shown in FIG. 10, the cassette system 500 has guide lines 504 drawn on the irradiated surface of a casing 502 as a reference mark for an image capturing area and an image capturing position. Using the guide lines 504, the subject to be imaged, such as the patient 14, can be positioned with respect to the cassette 24 and the range in which the radiation is to be applied to the cassette system 500 can be determined, for thereby recording radiation image information in an appropriate image capturing area of the cassette system 500.

The cassette system 500 also has a display unit 506 on the control unit 33 outside of the image capturing area thereof for displaying various items of information about the cassette system 500. Specifically, the display unit 506 displays ID information of the subject, e.g., the patient 14, whose radiation image is recorded in the cassette 24, the number of times that the cassette 24 has been used, an accumulated exposed dosage, the charged state (remaining power level) of the battery 44 housed in the control unit 33, image capturing conditions for radiation image information, and a positioning image representing the patient 14 positioned with respect to the cassette 24, etc. The radiological technician can confirm the patient 14 based on the ID information displayed on the display unit 506, also confirm in advance that the cassette system 500 is in a usable state, position the desired area of the patient 14 to be imaged with respect to the cassette 24 based on the displayed positioning image, and capture optimum radiation image information in the cassette system 500.

The cassette system 500 includes a handle 508 to be gripped by the user to handle and carry the cassette system 500 with ease.

The cassette system 500 also has an input terminal 510 for connection to an AC adapter, a USB (Universal Serial Bus) terminal 512, and a card slot 516 for receiving a memory card 514, all provided on a side wall of the casing of the cassette system 500.

When the charging function of the battery 44 housed in the cassette system 500 is low or when there is not enough time to charge the battery 44, an AC adapter is connected to the input terminal 510 to supply electric power from an external source for thereby making the cassette system 500 immediately operable.

The USB terminal 512 or the card slot 516 can be used when the cassette system 500 is unable to send and receive information to and from an external device such as the console 28 or the like by way of wireless communications. Specifically, when a USB cable connected to the external device is connected to the USB terminal 512, the cassette system 500 can send and receive information to and from the external device by way of wired communications through the USB terminal 512 and the USB cable. Alternatively, the memory card 514 is inserted into the card slot 516 and necessary information from the cassette system 500 is recorded into the memory card 514. Thereafter, the memory card 514 is removed from the card slot 516 and inserted into the external device to send the information to the external device.

The cassette system 500 is also capable of recording captured radiation image information while the control unit 33 and the cassette 24 are being spaced from each other. Accordingly, the amount of a radiation shield material such as a lead plate or the like used to shield the electronic components of the control unit 33 from the radiation is reduced, with the result that the cassette system 500 can be reduced in size and weight.

Figure 11:
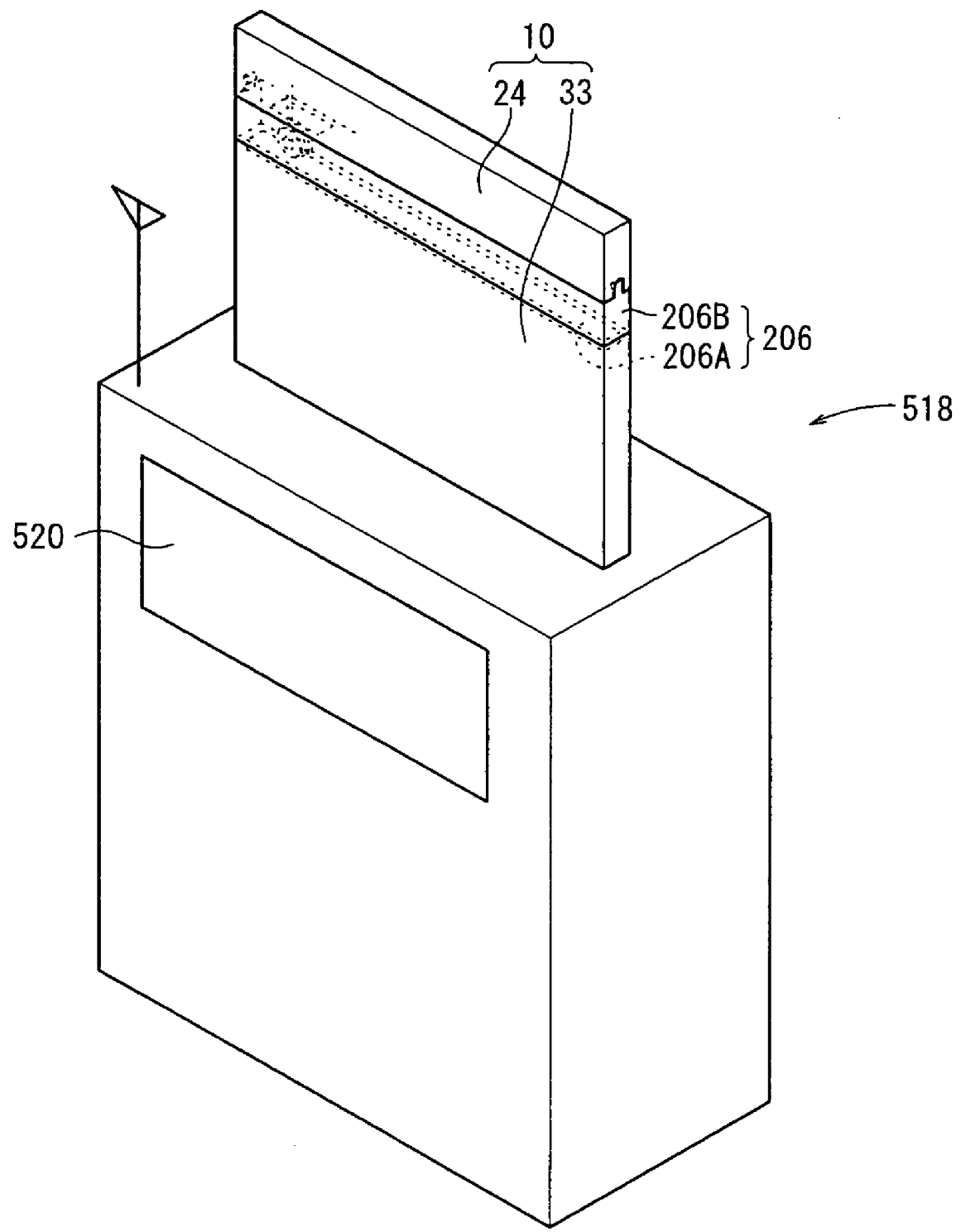
FIG. 11 is a perspective view of a cradle for charging a battery in the cassette system.
Figure 12:
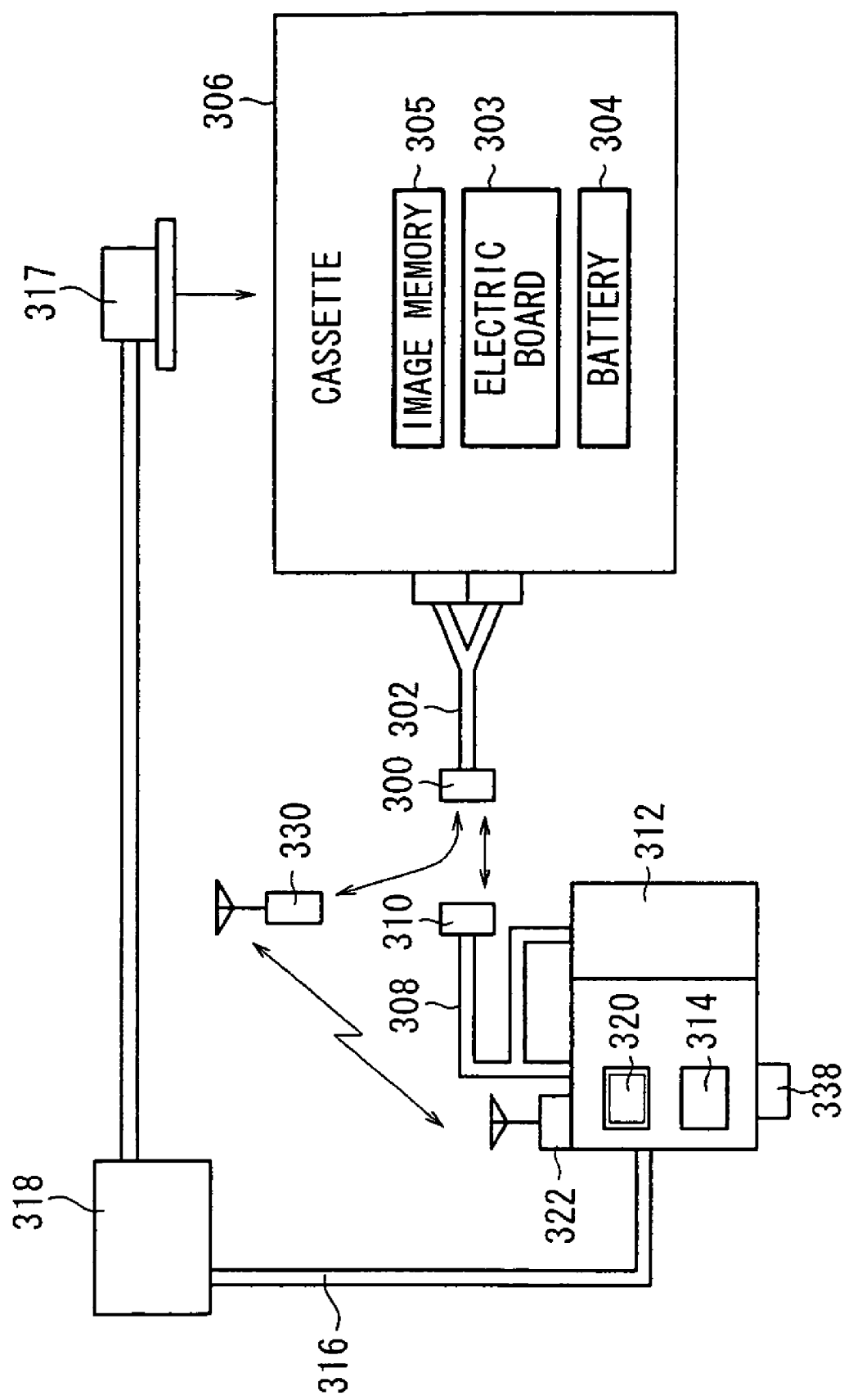
FIG. 12 is a block diagram of a radiation image capturing apparatus according to the related art.

FIG. 11 shows a cradle 518 for receiving the cassette system 10 and charging the battery 44 housed in the cassette system 10. The cradle 518 is positioned in the operating room 13 or a desired location in the hospital. The cradle 518 may not only be able to charge the battery 44, but also have a wireless or wired communication function to send and receive necessary information to and from an external device, such as the RIS 29, the HIS 31, the console 28, or the like. The information that is sent from and received by the cradle 518 may include radiation image information recorded in the cassette system 10 loaded in the cradle 518.

The cradle 518 has a display unit 520 for displaying the charged state of the battery 44 housed in the cassette system 10 and necessary information including radiation image information acquired from the cassette system 10.

A plurality of cradles 518 may be connected to a network, and charged states of the batteries 44 housed in the cassettes system 10 loaded in the respective cradles 518 may be retrieved through the network, so that the user can confirm the locations of any cassette systems 10 whose batteries 44 are sufficiently charged, based on the retrieved charged states of the batteries 44.

Although certain preferred embodiments of the present invention have been shown and described in detail, it should be understood that various changes and modifications may be made therein without departing from the scope of the appended claims.

What is claimed is:

1. A cassette system comprising:
a cassette having a radiation detector for detecting a radiation that has passed through a subject and converting the detected radiation into radiation image information; and a control unit which supplies electric power to said radiation detector and controls said radiation detector to receive said radiation image information therefrom, said control unit being detachably mounted on and separable from said cassette, wherein said control unit comprises a battery which supplies the electric power and a wireless unit which sends said radiation image information to an external control device by way of wireless communications, wherein said cassette and said control unit are connected to each other by a cable and at least one connector, and wherein said control unit is mechanically and directly integrated into said cassette by engaging a pair of engaging members while a radiation image of the subject is not captured, whereas said control unit is separated from but connected by the cable to said cassette while a radiation image of the subject is captured.

2. A cassette system according to claim 1, further comprising a take-up mechanism mounted on said control unit for winding up said cable such that said cable can be reeled out from said take-up mechanism.

3. A cassette system according to claim 1, wherein said control unit or said external control device includes a notifying unit for indicating electric field intensity information about the wireless communications.

4. A cassette system according to claim 1, wherein said control unit or said cassette includes a detecting unit for detecting whether said control unit is separate from said cassette or not.

5. A cassette system according to claim 4, wherein if said detecting unit detects that said control unit is not separate from said cassette, said control unit warns the external control device that said control unit is not separated from said cassette.

6. A cassette system according to claim 1, wherein said cassette further comprises a radiation shield and said control unit is devoid of said radiation shield.

7. A cassette system comprising: a cassette having a radiation detector for detecting a radiation that has passed through a subject and converting the detected radiation into radiation image information; and a control unit which supplies electric power to said radiation detector and controls said radiation detector to receive said radiation image information therefrom, said control unit being detachably mounted on and separable from said cassette, wherein said control unit comprises a battery which supplies the electric power and a wireless unit which sends said radiation image information to an external control device by way of wireless communications, wherein said cassette and said control unit are connected to each other by a cable and at least one connector, such that while detached said control unit, including the wireless unit, is connected by the cable to said cassette and is operative to be positioned by a user to optimize the wireless communications, and wherein said control unit is mechanically and directly integrated into said cassette by engaging a pair of engaging members while a radiation image of the subject is not captured.

8. A cassette system according to claim 1, wherein said control unit comprises a separation detecting unit for detecting whether said control unit is separated from said cassette or not.

9. A cassette system comprising: a cassette having a radiation detector for detecting a radiation that has passed through a subject and converting the detected radiation into radiation image information; and a control unit which supplies electric power to said radiation detector and controls said radiation detector to receive said radiation image information therefrom, said control unit being detachably mounted on and separable from said cassette; wherein said control unit comprises a battery which supplies the electric power and a wireless unit which sends said radiation image information to an external control device by way of wireless communications, wherein said cassette and said control unit are connected to each other by a cable and at least one connector, and wherein said control unit is separated from but connected by the cable to said cassette while a radiation image of the subject is captured and mechanically and directly integrated into said cassette by engaging a pair of engaging members while a radiation image of the subject is not captured.

10. A cassette system according to claim 9, further comprising a take-up mechanism mounted on said control unit for winding up said cable such that said cable can be reeled out from said take-up mechanism.

11. A cassette system according to claim 9, wherein said control unit or said external control device includes a notifying unit for indicating electric field intensity information about the wireless communications.

12. A cassette system according to claim 9, wherein said control unit or said cassette includes a detecting unit for detecting whether said control unit is separate from said cassette or not.

13. A cassette system according to claim 12, wherein if said detecting unit detects that said control unit is not separate from said cassette, said control unit warns the external control device that said control unit is not separated from said cassette.

14. A cassette system according to claim 9, wherein said cassette further comprises a radiation shield and said control unit is devoid of said radiation shield.

15. A cassette system according to claim 1, wherein the pair of engaging members includes a recess and a finger.

16. A cassette system according to claim 9, wherein the pair of engaging members includes a recess and a finger.

17. A cassette system according to claim 9, wherein the pair of engaging members includes a recess and a finger.

* * * * *